United States Patent [19]

Onizuka et al.

[11] Patent Number: 4,677,077
[45] Date of Patent: Jun. 30, 1987

[54] METHOD FOR MEASURING THE CONCENTRATION OF $CaCO_3$ IN A SLURRY

[75] Inventors: Masakazu Onizuka; Susumu Kono; Susumu Okino, all of Hiroshima, Japan

[73] Assignee: Mitsubishi Jukogyo Kabushiki Kaisha, Tokyo, Japan

[21] Appl. No.: 638,574

[22] Filed: Aug. 7, 1984

[30] Foreign Application Priority Data

Aug. 10, 1983 [JP] Japan ............... 58-144893

[51] Int. Cl.[4] ............ G01N 1/00; G01N 33/00; G01N 35/00
[52] U.S. Cl. .................. 436/50; 436/52; 436/55; 436/79; 436/133; 436/146; 436/175; 436/179; 436/181
[58] Field of Search ............. 436/43, 50, 51, 52, 436/55, 79, 127, 133, 146, 163, 174, 175, 177, 179, 181

[56] References Cited

U.S. PATENT DOCUMENTS

| | | | |
|---|---|---|---|
| 3,459,938 | 8/1969 | Stenger et al. | 436/146 |
| 3,801,281 | 4/1974 | Thompson et al. | 436/133 X |
| 4,046,510 | 9/1977 | Becker et al. | 436/146 |
| 4,061,467 | 12/1977 | Becker et al. | 436/179 X |
| 4,063,891 | 12/1977 | Becker et al. | 436/146 |
| 4,236,960 | 12/1980 | Hultman et al. | 436/55 X |
| 4,397,957 | 8/1983 | Allison | 436/133 |

FOREIGN PATENT DOCUMENTS 0096450 7/1980 Japan ............... 436/146

Primary Examiner—David L. Lacey
Assistant Examiner—Robert J. Hill, Jr.
Attorney, Agent, or Firm—Birch, Stewart, Kolasch and Birch

[57] ABSTRACT

A method for continuously measuring the concentration of $CaCO_3$ in slurries comprising $CaCO_3$ is described. The method comprises continuously sampling a given amount of the slurry, feeding the sampled slurry into an agitated continuous reactor container which is isolated from the outside air, keeping the slurry in the reactor container at a temperature of at least 50° C., adding sulfuric acid or hydrochloric acid to adjust the pH to below 4, blowing air into the slurry in the reactor container, withdrawing from the reactor container $CO_2$, produced by the reaction between $CaCO_3$ and the acid, by entrainment with the air, and calculating the concentration of $CaCO_3$ in the slurry from the concentration of $CO_2$ in the withdrawn gas, the amount of the sampled slurry and the flow rate of the blown air.

5 Claims, 4 Drawing Figures

F I G. 2(a)
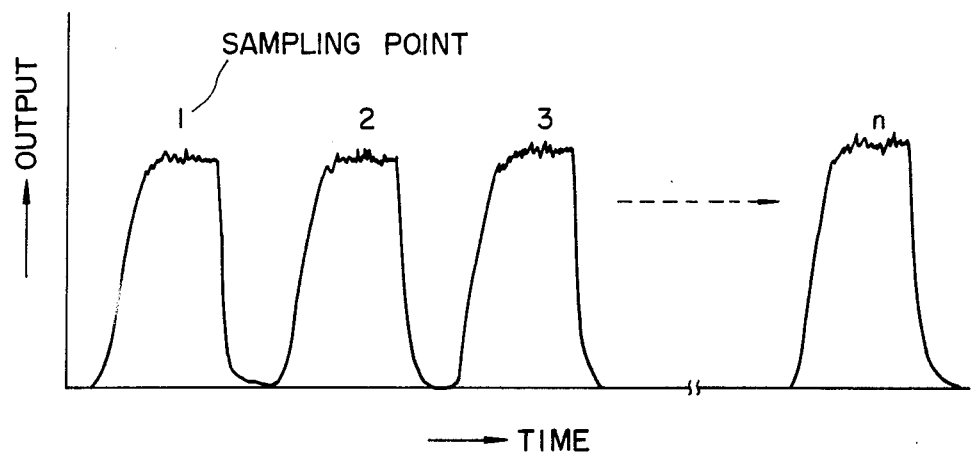
F I G. 2(b)
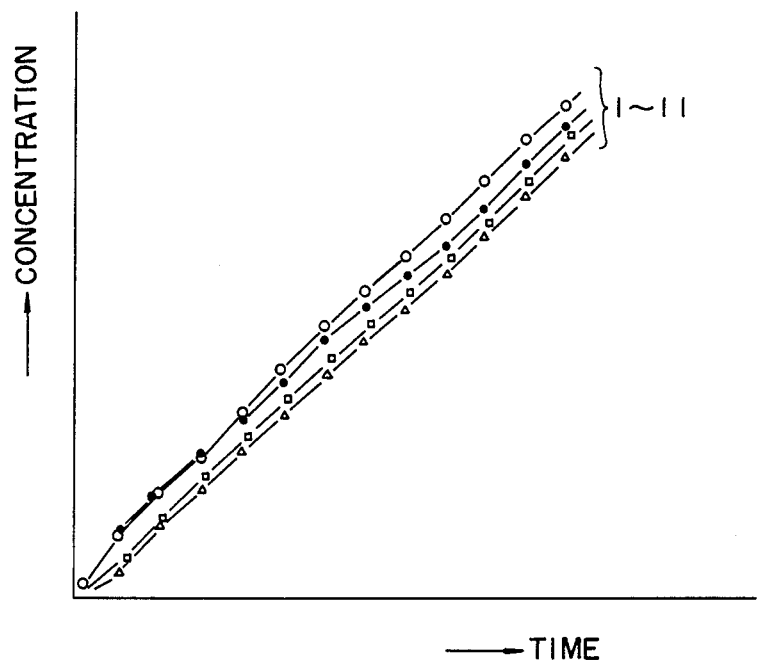

1

METHOD FOR MEASURING THE CONCENTRATION OF CACO3 IN A SLURRY

BACKGROUND OF THE INVENTION

1. Field of the Invention

This invention relates to a method for continuously measuring a concentration of $CaCO_3$ in slurries comprising $CaCO_3$ such as, for example, an absorption liquid slurry used in flue gas desulfurization systems using a wet lime process.

2. Description of the Prior Art

The concentration of $CaCO_3$ in an absorption solution used in flue gas desulfurization systems using a wet lime process has been heretofore measured by manual analysis. This manual analysis is disadvantageous in requiring hands and time.

SUMMARY OF THE INVENTION

The present invention is accomplished to overcome the above disadvantages. This object is achieved, according to the present invention, by a method for continuously measuring the concentration of $CaCO_3$ in slurries comprising $CaCO_3$, the method comprising:
continuously sampling a given amount of the slurry;
feeding the sampled slurry into an agitated continuous reactor container which is isolated from the outside air;
keeping the slurry at a temperature of at least 50° C.;
adding sulfuric acid or hydrochloric acid to adjust the pH to below 4;
blowing air into the slurry in the reactor container;
withdrawing from the reactor container $CO_2$, produced by the reaction between $CaCO_3$ and the acid, by entrainment with the air; and
calculating the concentration of $CaCO_3$ in the slurry from the concentration of $CO_2$ in the mixed gas, the amount of the sampled slurry, and the flow rate of the blown air. The method may further comprise the steps of mixing the withdrawn gas with air, and calculating the concentration of $CaCO_3$ in the slurry from the concentration of $CO_2$ in the mixed gas, the flow rate of the sampled slurry, the flow rate of the blown air, and the flow rate of the air being mixed.

BRIEF DESCRIPTION OF THE DRAWINGS

FIGS. 2(a) and 2(b) are graphical representations of the results of the measurement according to one embodiment of the invention.

DETAILED DESCRIPTION AND EMBODIMENTS OF THE INVENTION

Figure 1:
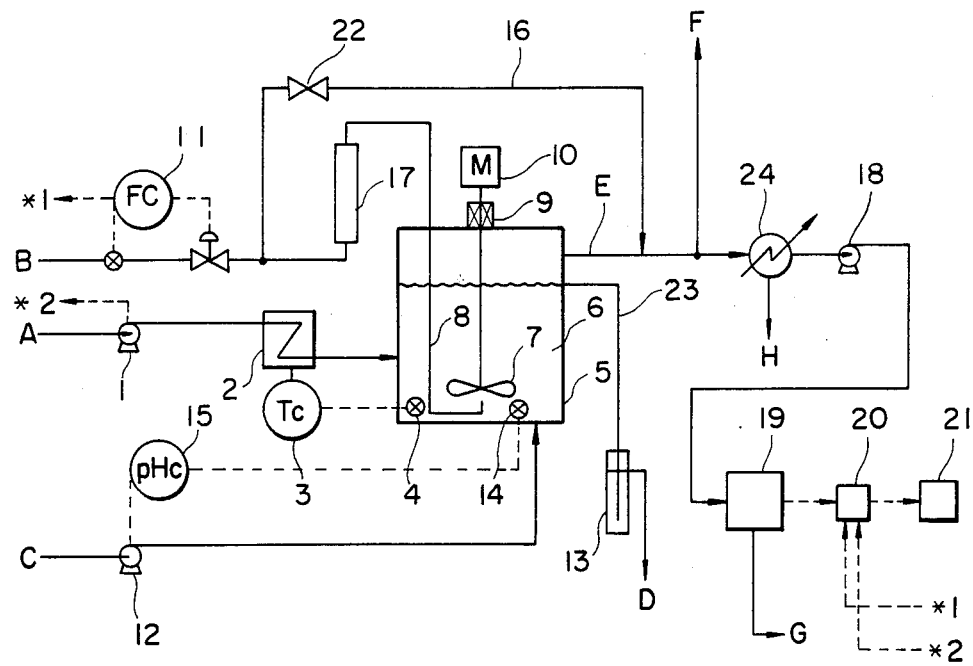
FIG. 1 is a flowchart of an apparatus for measuring a concentration of $CaCO_3$ according to the invention.

Reference is now made to FIG. 1 which illustrates one embodiment of the invention.

In FIG. 1, sample slurry A comprising $CaCO_3$ is sampled by a fixed displacement pump 1 and is heated through the heater 2 which is controlled by a signal from temperature controller 3 after detection of a temperature of a resident liquid 6 in a reactor container 5 with a detector 4 so that the temperature of the resident liquid 6 is kept at a predetermined temperature, followed by feeding to the reactor container 5. In view of the detection efficiency of $CaCO_3$, the temperature of the resident liquid 6 is preferred to be over 50° C., inclusive, with the upper limit to a boiling point of the liquid.

The pH of the liquid 6 in the reactor container 5 is checked by the use of a pH detector 14 and a delicate pump 12 is controlled by the signal from the pH adjuster 15, by which sulfuric acid (or hydrochloric acid) is introduced into the reactor container 5 and the pH in the system is adjusted to a predetermined level (below 4).

It will be noted that the upper limit of the temperature of the resident liquid 6 is a boiling point of the resident liquid and the pH is preferably controlled to be in the range of from 2 to 4.

During the operation, $CO_2$ is generated according to the following reaction (1) or (2).

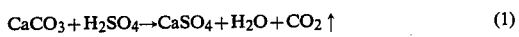
$$CaCO_3 + H_2SO_4 \rightarrow CaSO_4 + H_2O + CO_2 \uparrow \quad (1)$$

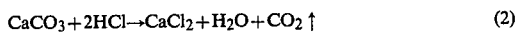
$$CaCO_3 + 2HCl \rightarrow CaCl_2 + H_2O + CO_2 \uparrow \quad (2)$$

In order to smoothly remove the generated $CO_2$, part or all of air B whose flow rate is controlled at a given level by means of a flow controller 11 is blown into the resident liquid through a flow indicator 17 and an air blowing pipe 8 by manupilation of a distributing valve 22. During this operation, the resident liquid 6 is agitated by means of an agitator 7 driven through a sealing material 9 by a motor 10 so that the solid matters contained in the resident liquid 6 in the reactor container 5 do not settle.

An excess of the resident liquid 6 caused by the feed of sample slurry A from the fixed displacement pump 1 is discharged from an overflow pipe 23 into a liquid sealing device 13. The sealing device 13 is kept at a depth of the liquid which can overcome the inner pressure of the reactor container 5, thus preventing leakage of the $CO_2$-containing gase E (withdrawn gas) in the reactor container 5 by entrainment with the overflow. In addition, the sealing device 13 is so designed that the solid matters in the overflow do not settle. The excess of the overflow charged into the liquid sealing device 13 is discharged as waste liquor D.

The mixed gas (withdrawn gas) E consisting of the $CO_2$ generated according to the reaction equation (1) or (2) and the air and evaporated moisture from the air blowing pipe 8 is combined with air which flows through a bypath of the reactor 6 is released as exhaust F. In this connection, part of the exhaust F is subjected to a dehumidifier 24 to remove the moisture therefrom as drain H, then sucked by an air pump 18 and fed to a $CO_2$ analyzer 19 in which the concentration of $CO_2$ in the exhaust is measured, followed by discharging as exhaust G. The reason why the air 16 is combined with the mixed gas E is that the gas E is diluted to a level at which the detection with the $CO_2$ analyzer becomes possible. No dilution is necessary when the $CO_2$ analyzer 19 has great capability of detection.

The detection signal from the $CO_2$ analyzer 19 is fed to is fed to an operator 20 for calculation of a concentration of $CaCO_3$ in the sampled slurry A. To the operator 21 are also inputted flow signal *1 from the air flow meter 11 and flow signal *2 from the fixed displacement pump 1 for the sampling of slurry. These three input signas are logically operated in the operator 20 according to the following equation, thereby determining a concentration of $CaCO_3$ in the sampled slurry A. The concentration of $CaCO_3$ is indicated by a $CaCO_3$ concentration indicator 21.

$$\text{Concentration of } CaCO_3 \text{ [mol/l]} = \frac{Q \times X}{(100 - X) \times 22.4 \times F} \quad (3)$$

Q: flow rate of air [Nl/min]
F: flow rate of slurry being sampled [l/min]
X: concentration of $CO_2$ [vol%]

As described before, according to the invention, it is possible to continuously detect a concentration of $CaCO_3$ in slurry.

The present invention is more particularly described by way of example.

EXAMPLE

A test plant shown in FIG. 1 was used to effect a continuous measurement of a concentration of $CaCO_3$ in a $CaCO_3$-containing slurry under the following conditions:

Concentration of $CaCO_3$ in sample slurry: 0.05, 0.1, 0.2 mol/l
Amount of sampled slurry: 0.12 l/min
Flow rate of blown air: 7 Nl/min
Setting of reaction temperature: 50° C.
Setting of pH for reaction: 4
Preset concentration of $CO_2$: 2 vol%
Total flow rate of air: 20 Nl/min
Reactor container: 1 liter in capacity The results of the measurement are shown in FIGS. 2(a) and 2(b).

Figure 3:
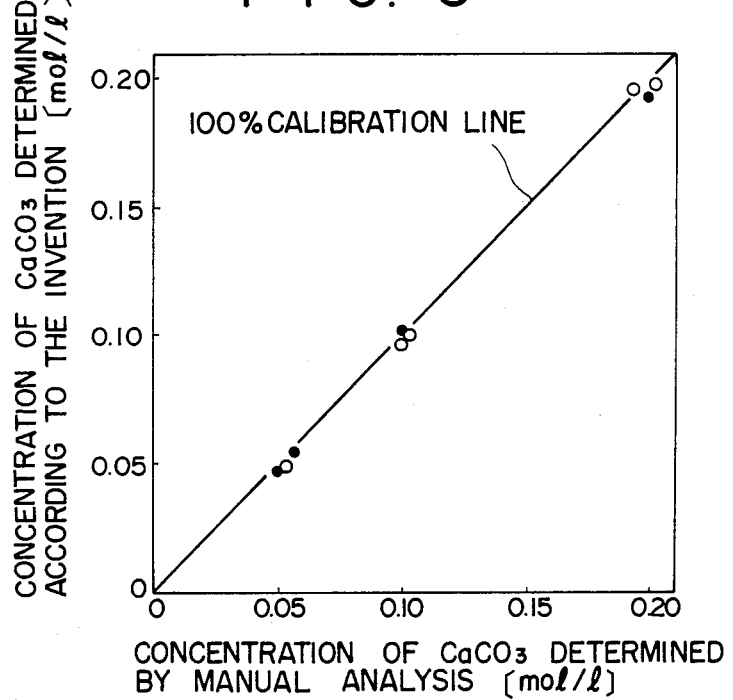
FIG. 3 is a graphical representation of the relationship between measured value of $CaCO_3$ concentration (mol/vol) determined according to the method of the invention and value determined by known manual analysis.

In FIG. 3, the values detected by the method of the invention are indicated as circles in relation to the analytical values obtained by known manual analysis, in which the mark "solid circle" indicates the results using hydrochloric acid and the mark "simple circle" indicates the results using sulfuric acid.

The test was effected using three different concentrations of $CaCO_3$ in slurry, and typical results of the measured value of $CO_2$, manually analytical value of $CaCO_3$, and value of $CaCO_3$ detected according to the invention are shown in the following table.

| | | Test No. | | |
|---|---|---|---|---|
| | | 1 | 2 | 3 |
| Concentration of $CaCO_3$ by manual analysis | mol/l | 0.056 | 0.104 | 0.192 |
| Concentration of $CaCO_3$ according to invention | mol/l | 0.053 | 0.100 | 0.195 |
| Concentration of $CO_2$ | % | 0.71 | 1.32 | 2.55 |
| Acid used | | HCl | $H_2SO_4$ | $H_2SO_4$ |

As will be appreciated from the foregoing, according to the invention, it becomes possible to accurately measure a concentration of $CaCO_3$ in slurry in a continuous manner.

What is claimed is:

1. A method for continuously measuring the concentration of $CaCO_3$ in a slurry containing $CaCO_3$ which is used in flue gas desulfurization systems using a wet lime process, the steps consisting essentially of:
   continuously sampling a given amount of the slurry;
   feeding the sampled slurry at a predetermined flow rate into an agitated continuous reactor container having a bottom and which is isolated from outside air;
   keeping the slurry in the reactor container at a temperature of at least 50° C.;
   adding an acid to the reactor container to adjust the pH of the slurry therein to below 4;
   blowing air into the slurry in the reactor container at a predetermined flow rate;
   withdrawing gas from the reactor container wherein the withdrawn gas comprises the blown air with $CO_2$ produced by a reaction between $CaCO_3$ and the acid entrained therein measuring the concentration of $CO_2$ in the withdrawn gas; and
   calculating the concentration of $CaCO_3$ in the slurry from the $CO_2$ concentration in the withdrawn gas, the flow rate of the sampled slurry, and the flow rate of said blown air.

2. The method according to claim 1, wherein the pH of the slurry in the reactor container is adjusted to between 2 to 4.

3. The method according to claim 1, wherein the acid is selected from the group consisting of sulfuric acid and hydrochloric acid.

4. The method according to claim 1, wherein the slurry in the reactor container is maintained at a temperature in the range of from 50° C. to the boiling point of the slurry in the reactor container.

5. The method according to claim 1, wherein the blown air enters the reactor container from the bottom of said reactor container, dilution air is added to the withdrawn gas at a predetermined flow rate prior to the step of measuring the $CO_2$ concentration in the withdrawn gas, and wherein the calculating step comprises calculating the concentration of $CaCO_3$ in the slurry from the $CO_2$ concentration in the withdrawn gas, the flow rate of the sampled slurry, the flow rate of the blown air and the flow rate of the dilution air.

* * * * *